United States Patent [19]  [11] 4,153,699
Farge et al.  [45] * May 8, 1979

[54] THIAZOLO[3,4-A]INDOLE DERIVATIVES AND PHARMACEUTICAL COMPOSITIONS CONTAINING THEM

[75] Inventors: Daniel Farge, Thiais; Alain Jossin, Saint Cloud; Gerard Ponsinet, Sucy-en-Brie; Daniel Reisdorf, Thiais, all of France

[73] Assignee: Rhone-Poulenc Industries, Paris, France

[*] Notice: The portion of the term of this patent subsequent to Dec. 20, 1994, has been disclaimed.

[21] Appl. No.: 871,133

[22] Filed: Jan. 20, 1978

[30] Foreign Application Priority Data

Feb. 4, 1977 [FR] France .................................. 77 03186
Dec. 23, 1977 [FR] France .................................. 77 39029

[51] Int. Cl.² .................... A61K 31/47; A61K 31/44; C07D 513/14
[52] U.S. Cl. .................................. 424/258; 424/263; 546/143; 546/270
[58] Field of Search ...... 260/283 S, 288 CE, 294.8 B; 424/258, 263

[56] References Cited

U.S. PATENT DOCUMENTS 3,819,618  6/1974  Haugwitz et al. ............... 260/240 F
4,064,247  12/1977  Farge et al. .......................... 424/258

Primary Examiner—Donald G. Daus
Assistant Examiner—Diana G. Rivers
Attorney, Agent, or Firm—Stevens, Davis, Miller & Mosher

[57] ABSTRACT

Compounds of the formula:

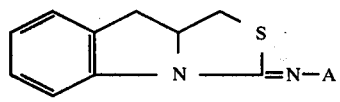

wherein A represents a heterocyclic radical selected from 3-pyridyl, 4-pyridyl, 5-isoquinolyl and 5-isoquinolyl substituted in the 3-position by an alkyl radical containing 1 to 10 carbon atoms, are new compounds possessing pharmacological properties, in particular analgesic, antipyretic and anti-inflammatory properties.

8 Claims, No Drawings

THIAZOLO[3,4-A]INDOLE DERIVATIVES AND PHARMACEUTICAL COMPOSITIONS CONTAINING THEM

This invention relates to new therapeutically useful thiazolo[3,4-a]indole derivatives, to a process for their preparation and to pharmaceutical compositions containing them.

The new thiazolo[3,4-a]indole derivatives of the present invention are those of the general formula:

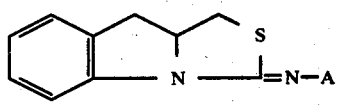
I wherein A represents a heterocyclic radical selected from 3-pyridyl, 4-pyridyl, 5-isoquinolyl and 5-isoquinolyl substituted in the 3-position by a straight- or branched-chain alkyl radical containing 1 to 10 carbon atoms, and acid addition salts thereof.

The compounds of general formula I can exist in (R) and (S) forms and the invention includes both such forms and mixtures thereof.

According to a feature of the present invention, the thiazolo[3,4-a]indole derivatives of general formula I are prepared by the process which comprises the reaction of an amine of the general formula:

$H_2N-A$   II (wherein A is as hereinbefore defined) with a salt of the general formula:

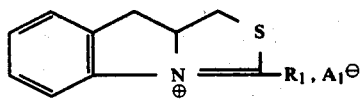
III wherein $R_1$ represents a chlorine atom, an alkylthio radical containing from 1 to 4 carbon atoms (preferably methylthio) or a benzylthio radical, and $A_1^{\ominus}$ represents an anion such as a chloride, iodide, sulphate, tetrafluoroborate or fluorosulphonate ion.

When $R_1$ represents a chlorine atom, $A_1^{\ominus}$ represents a chloride ion. When $R_1$ represents an alkylthio or benzylthio radical, $A_1^{\ominus}$ represents an iodide, sulphate, tetrafluoroborate or fluorosulphonate ion.

When $R_1$ represents a chlorine atom and $A_1^{\ominus}$ represents a chloride ion, the reaction is preferably carried out in an organic solvent, such as acetonitrile, in the presence of an alkaline condensation agent, such as triethylamine, at a temperature of about 20° C.

When $R_1$ represents an alkylthio or benzylthio radical and $A_1^{\ominus}$ represents an iodide, sulphate, tetrafluoroborate or fluorosulphonate ion, the reaction is preferably carried out in a basic organic solvent, such as pyridine, at a temperature of about 20° C.

The salt of general formula III wherein $R_1$ represents a chlorine atom and $A_1^{\ominus}$ represents a chloride ion can be obtained by the reaction of a chlorinating agent, such as phosgene, phosphorus pentachloride, thionyl chloride or oxalyl chloride, on 9,9a-dihydrothiazolo[3,4-a]indole-3-thione of the formula:

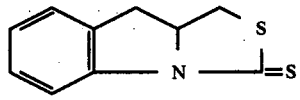
IV

The reaction is generally carried out in an organic solvent or in a mixture of organic solvents, such as a mixture of toluene and tetrahydrofuran, at a temperature between 0° and 70° C.

The salts of general formula III wherein $R_1$ represents an alkylthio or benzylthio radical and $A_1^{\ominus}$ represents an iodide, sulphate, tetrafluoroborate or fluorosulphonate ion, can be obtained by the reaction of a reactive ester of the general formula:

$R_2-A_1$   V (wherein $R_2$ represents an alkyl radical containing 1 to 4 carbon atoms or a benzyl radical, and $A_1$ represents the residue of a reactive ester such as an iodine atom or an alkoxysulphonyloxy radical), or of triethyloxonium tetrafluoroborate or methyl fluorosulphonate, with a compound of general formula IV. The reaction is generally effected, optionally in the presence of an organic solvent such as methylene chloride, at a temperature of about 20° C.

9,9a-Dihydrothiazolo[3,4-a]indole-3-thione of formula IV can be obtained by the reaction of carbon disulphide in a basic medium with an indoline of the general formula:

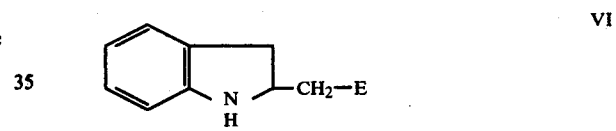
VI wherein E represents a halogen, e.g. bromine or chlorine, atom or a hydroxysulphonyloxy radical. The reaction is generally carried out in an aqueous medium in the presence of sodium or potassium hydroxide at a temperature of about 20° C.

The compounds of general formula VI can be obtained by the action of an inorganic acid on 2-hydroxymethylindoline of the formula:

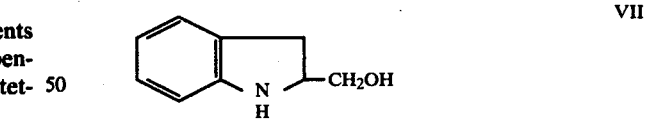
VII

The compound of general formula VI wherein E represents the hydroxysulphonyloxy radical is prepared by treatment of the indoline compound of formula VII with sulphuric acid in an aqueous medium at a temperature of about 160° C. or in an organic solvent (such as dimethylformamide) in the presence of dicyclohexylcarbodiimide at a temperature of about 20° C.

The compound of general formula VI wherein E represents the bromine atom is prepared by treatment of the compound of formula VII with a concentrated aqueous solution of hydrogen bromide (at least 40% and preferably 48% by weight) at the reflux temperature of the reaction mixture, and isolation of the product of general formula VI as its hydrobromide.

The compound of general formula VI wherein E represents the chlorine atom is generally prepared by treatment of the compound of formula VII with thionyl chloride in an organic solvent, such as chloroform saturated with hydrogen chloride gas, at the reflux temperature of the reaction mixture, and isolation of the product of formula VI as its hydrochloride.

The indoline derivative of formula VII can be prepared starting with ethyl indole-2-carboxylate of the formula:

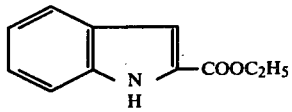

VIII by application of the method described by E. J. Corey et al., J. Amer. Chem. Soc., 92, 2476 (1970).

The amines of general formula II wherein A represents a 5-isoquinolyl radical substituted in the 3-position by a straight- or branched-chain alkyl radical containing 1 to 10 carbon atoms can be obtained starting from a 3-alkylisoquinoline of the general formula:

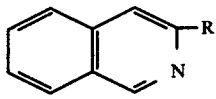

IX (wherein R represents a straight- or branched-chain alkyl radical containing from 1 to 10 carbon atoms) by application of the method described by N. P. Buu Hoï et al., J. Chem. Soc. 3924 (1964).

The isoquinoline derivatives of general formula IX can be obtained according to the method described by J. Murakoshi et al., Yakugaku Zasshi 79, 1578 (1959), or by the method described by F. Damerow, Ber. 27, 2232 (1894).

The thiazolo[3,4-a]indole derivatives of general formula I may be converted by known methods into acid addition salts. The acid addition salts may be obtained by the action of acids on the thiazolo[3,4-a]indole derivatives in appropriate solvents. As organic solvents there may be used alcohols, ketones, ethers or chlorinated hydrocarbons. The salt which is formed is precipitated, if necessary after concentrating the solution, and is isolated by filtration or by decantation. By the term "known methods" as employed in this specification is meant methods heretofore used or described in the chemical literature.

The thiazolo[3,4-a]indole derivatives of general formula I and/or their acid addition salts can optionally be purified by physical methods such as crystallisation or chromatography.

The thiazolo[3,4-a]indole derivatives of general formula I and their acid addition salts possess useful pharmacological properties. They are particularly active as analgesic, antipyretic and anti-inflammatory agents.

The analgesic activity is demonstrated in rats at doses of between 2 and 50 mg/kg animal body weight administered orally using the technique of L. O. Randall and J. J. Selitto, Arch. Int. Pharmacodyn., 111, 409 (1957), modified by K. F. Swingle et al., Proc. Soc. Exp. Biol. Med., 137, 536 (1971).

The antipyretic activity is demonstrated in rats at doses of between 2 and 20 mg/kg animal body weight administered orally using the technique of J. J. Loux et al., Toxicol. Appl. Pharmacol., 22, 674 (1972).

The anti-inflammatory activity is demonstrated in rats at doses of between 5 and 250 mg/kg animal body weight administered orally when using the technique of K. F. Benitz and L. M. Hall, Arch. Int. Pharmacodyn., 144, 185 (1963).

Moreover, the 50% lethal dose ($LD_{50}$) of the compounds according to the invention is between 300 and 900 mg/kg animal body weight when administered orally to mice or greater than the aforementioned higher dosage.

For therapeutic purposes, the thiazolo[3,4-a]indole derivatives of general formula I may be employed as such or in the form of pharmaceutically acceptable acid addition salts, that is to say salts which are non-toxic at the doses used for therapy. Suitable acid addition salts are hydrochlorides, sulphates, nitrates, phosphates, acetates, propionates, succinates, benzoates, fumarates, maleates, tartrates, theophyllinacetates, salicylates, phenolphthalinates and methylene-bis-β-hydroxynaphthoates.

The thiazolo[3,4-a]indole derivatives of general formula I wherein A represents 3-pyridyl, 4-pyridyl or 5-isoquinolyl, or a 5-isoquinolyl radical substituted in the 3-position by an alkyl radical containing 1 to 3 carbon atoms, are of particular interest.

The following non-limitative Examples illustrate the preparation of thiazolo[3,4-a]indole derivatives of the present invention.

EXAMPLE 1

(RS)-3-Methylthio-9,9a-dihydrothiazolo[3,4-a]indolium iodide (14.0 g) is added to a solution of 3-aminopyridine (4.5 g) in pyridine (150 cc). The suspension gradually passes into solution. After 24 hours at a temperature of about 20° C., the mixture is concentrated to dryness under reduced pressure (25 mm Hg) at 50° C. The residue is dissolved in a mixture of methylene chloride (500 cc) and 2 N aqueous sodium hydroxide solution (150 cc). The organic phase is decanted, washed with water (200 cc), dried over magnesium sulphate, filtered and then concentrated to dryness under reduced pressure (40 mm Hg) at 40° C. The residue obtained is recrystallised from absolute ethanol (40 cc). (RS)-3-(Pyrid-3-ylimino)-9,9a-dihydrothiazolo[3,4-a]indole (8.2 g), melting at 131° C., is obtained.

(RS)-3-Methylthio-9,9a-dihydrothiazolo[3,4-a]indolium iodide can be prepared as follows:

Methyl iodide (40 cc) is added to a solution of (RS)-9,9a-dihydrothiazolo[3,4-a]indole-3-thione (30.0 g) in methylene chloride (150 cc). After stirring for 20 hours at about 20° C., the resulting crystals are filtered off, washed with diethyl ether (2×50 cc) and then dried at 20° C. under reduced pressure (20 mm Hg). (RS)-3-Methylthio-9,9a-dihydrothiazolo[3,4-a]indolium iodide (50.2 g), melting at 135°–140° C. with decomposition, is thus obtained.

(RS)-9,9a-Dihydrothiazolo[3,4-a]indole-3-thione can be prepared as follows:

Carbon disulphide (65 cc) is added to a suspension of (RS)-2-hydroxysulphonyloxymethylindoline (45.8 g) in 1.5 N aqueous sodium hydroxide solution (400 cc). After stirring for 2 hours at a temperature of about 20° C., a solution is obtained and the formation of beige crystals is then observed; stirring is continued for 12 hours. The crystals formed are filtered off, washed with water and then recrystallised from ethanol (850 cc). (RS)-9,9a-dihydrothiazolo[3,4-a]indole-3-thione (31.3 g) is thus obtained in the form of white crystals melting at 132° C.

(RS)-2-Hydroxysulphonyloxymethylindoline can be prepared as follows:

(RS)-2-Hydroxymethylindoline (29.8 g) is dissolved in a mixture of 34 N sulphuric acid (11.5 cc) and water (60 cc). The mixture is heated whilst distilling the water under reduced pressure (10 mm Hg), the heating bath being raised gradually to 160° C., which temperature is maintained for 2 hours. (RS)-2-Hydroxysulphonyloxymethylindoline (45.8 g) is thus obtained in the form of white crystals.

(RS)-2-Hydroxymethylindoline can be prepared in accordance with the method of E. J. Corey et al., J. Amer. Chem. Soc., 92, 2476 (1970).

EXAMPLE 2

Following the procedure of Example 1 but starting with 5-amino-3-methylisoquinoline (6.0 g) and (S)-3-methylthio-9,9a-dihydrothiazolo[3,4-a]indolium iodide (12.0 g), (S)-3-[(3-methylisoquinol-5-yl)imino]-9,9a-dihydrothiazolo[3,4-a]indole (8.3 g) is obtained, after recrystallisation from ethanol, in the form of white crystals melting at 182° C. $[\alpha]_D^{20} = -92.5 \pm 1.5°$ (c=1, chloroform)

EXAMPLE 3

Following the procedure of Example 1 but starting with 5-amino-3-methylisoquinoline (5.7 g) and (R)-3-methylthio-9,9a-dihydrothiazolo[3,4-a]indolium iodide (11.4 g), (R)-3-[(3-methylisoquinol-5-yl)imino]-9,9a-dihydrothiazolo[3,4-a]indole (7.3 g) is obtained, after recrystallisation from ethanol, in the form of white crystals melting at 181° C. $[\alpha]_D^{20} = +92.0 \pm 1.5°$ (c=1, chloroform)

EXAMPLE 4

(RS)-3-Methylthio-9,9a-dihydrothiazolo[3,4-a]indolium iodide (17.5 g) is added to a solution of 4-aminopyridine (7.0 g) in pyridine (200 cc). The suspension gradually passes into solution. After 18 hours at a temperature of about 20° C., the mixture is concentrated to dryness under reduced pressure (25 mm Hg). The residue is dissolved in a mixture of methylene chloride (400 cc) and 2 N aqueous sodium hydroxide solution (200 cc). The organic phase is decanted, washed with water, dried over magnesium sulphate, filtered and then concentrated to about 100 cc under reduced pressure.

This solution is poured over a column (column diameter: 3 cm) of silica (300 g) and elution is carried out with methylene chloride (2400 cc) followed by a mixture of methylene chloride and methanol (99.3:0.7 by volume; 6000 cc), eluate fractions of 200 cc being collected. After evaporating fractions 20 to 40, (RS)-3-(pyrid-4-ylimino)-9,9a-dihydrothiazolo[3,4-a]indole (6.9 g) is obtained in the form of white crystals which, after recrystallisation from acetonitrile, melt at 140° C.

EXAMPLE 5

Following the procedure of Example 1 but starting with 5-aminoisoquinoline (4.2 g) and (RS)-3-methylthio-9,9a-dihydrothiazolo[3,4-a]indolium iodide (9.3 g), (RS)-3-(isoquinol-5-ylimino)-9,9a-dihydrothiazolo[3,4-a]indole (5.0 g), melting at 142° C., is obtained after crystallisation of the product from heptane (250 cc) and recrystallisation from acetonitrile (50 cc).

EXAMPLE 6

Following the procedure of Example 1 but starting with 5-amino-3-methyl-isoquinoline (8.7 g) and (RS)-3-methylthio-9,9a-dihydro-thiazolo[3,4-a]indolium iodide (17.5 g), (RS)-3-[(3-methylisoquinol-5-yl)imino]-9,9a-dihydrothiazolo[3,4-a]indole (11.4 g), is obtained, after recrystallisation from ethanol, in the form of white crystals melting at 182° C.

EXAMPLE 7

Following the procedure of Example 1 but starting with 5-amino-3-ethylisoquinoline (3.3 g) and (RS)-3-methylthio-9,9a-dihydrothiazolo[3,4-a]indolium iodide (6.3 g), (RS)-3-[(3-ethylisoquinol-5-yl)imino]-9,9a-dihydrothiazolo[3,4-a]indole (4.4 g) is obtained, after recrystallisation from ethanol (40 cc), in the form of white crystals melting at 142° C.

The present invention includes within its scope pharmaceutical compositions comprising, as active ingredient, at least one of the compounds of general formula I, or a non-toxic acid addition salt thereof, in association with at least one compatible and pharmaceutically acceptable carrier. The invention includes especially such preparations made up for oral, parenteral, rectal or local administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration also include capsules of absorbable material such as gelatin containing the active substance with or without the addition of diluents or excipients.

Preparations according to the invention for parenteral administration include sterile non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions which can be dissolved in a sterile injectable medium immediately before use.

Compositions for rectal administration are suppositories which contain, in addition to the active substance, excipients such as cacao butter or a suitable wax base.

Compositions for local administration can be, for example, in the form of ointments.

The percentage of active ingredient in the compositions of the invention may be varied, it being necessary that it should constitute a proportion such that a suitable dosage shall be obtained.

The compositions according to the invention are particularly useful in human therapy by virtue of their analgesic, antipyretic and anti-inflammatory action. They are particularly suitable for the treatment of acute and chronic pains, rheumatic and traumatic algias, dental, neurological and visceral pains, various algias (pains experienced by cancer patients), febrile conditions, and inflammatory diseases (ankylosing spondylarthritis, acute articular rheumatism and arthrosis). In human therapy, the doses depend on the desired effect and on the duration of the treatment; they are generally between 150 and 2000 mg per day for an adult.

In general terms, the physician will decide the posology which he considers to be most appropriate, taking into account the age, weight and any other factors intrinsic to the patient being treated.

The following Example illustrates pharmaceutical compositions according to the invention.

EXAMPLE 8

Tablets containing the active product (100 mg) and having the following composition are prepared in accordance with the usual technique:

| | |
|---|---|
| (RS)-3-[(3-methylisoquinol-5-yl)imino]-9,9a-dihydrothiazolo[3,4-a]indole | 0.100 g |
| starch | 0.110 g |
| precipitated silica | 0.035 g |
| magnesium stearate | 0.005 g |

We claim:
1. A thiazolo[3,4-a]indole derivative of the formula:

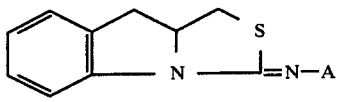

wherein A represents a heterocyclic radical selected from 3-pyridyl, 4-pyridyl, 5-isoquinolyl and 5-isoquinolyl substituted in the 3-position by alkyl of 1 through 10 carbon atoms, and non-toxic pharmaceutically acceptable acid addition salts thereof.

2. A thiazolo[3,4-a]indole derivative according to claim 1 wherein A represents 3-pyridyl, 4-pyridyl, 5-isoquinolyl or 5-isoquinolyl substituted in the 3-position by alkyl of 1 through 3 carbon atoms, and non-toxic pharmaceutically acceptable acid addition salts thereof.

3. A compound according to claim 1 which is 3-(pyrid-3-ylimino)-9,9a-dihydrothiazolo[3,4-a]indole and its non-toxic pharmaceutically acceptable acid addition salts.

4. A compound according to claim 1 which is 3-[(3-methylisoquinol-5-yl)imino]-9,9a-dihydrothiazolo-[3,4-a]indole and its non-toxic pharmaceutically acceptable acid addition salts.

5. A compound according to claim 1 which is 3-(pyrid-4-ylimino)-9,9a-dihydrothiazolo[3,4-a]indole and its non-toxic pharmaceutically acceptable acid addition salts.

6. A compound according to claim 1 which is 3-(isoquinol-5-ylimino)-9,9a-dihydrothiazolo[3,4-a]indole and its non-toxic pharmaceutically acceptable acid addition salts.

7. A compound according to claim 1 which is 3-[(3-ethylisoquinol-5-yl)imino]-9,9a-dihydrothiazolo-[3,4-a]indole and its non-toxic pharmaceutically acceptable acid addition salts.

8. A pharmaceutical composition useful as an antipyretic, anti-inflammatory and analgesic agent, which comprises as active ingredient an effective amount of a thiazolo[3,4-a]-indole derivative as claimed in claim 1, or a non-toxic pharmaceutically acceptable acid addition salt thereof, in association with a significant amount of a pharmaceutically acceptable carrier.

* * * * *